(12) United States Patent
Chu et al.

(10) Patent No.: US 7,371,228 B2
(45) Date of Patent: May 13, 2008

(54) DELIVERY OF THERAPEUTICS TO TREAT ANEURYSMS

(75) Inventors: Jack Chu, Santa Rosa, CA (US); Dave Erickson, Santa Rosa, CA (US); Prema Ganesan, San Francisco, CA (US); Jonathan Morris, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 417 days.

(21) Appl. No.: 10/665,936

(22) Filed: Sep. 19, 2003

(65) Prior Publication Data
US 2005/0065593 A1 Mar. 24, 2005

(51) Int. Cl.
*A61K 9/22* (2006.01)
*A61F 13/00* (2006.01)
*A61M 31/00* (2006.01)

(52) U.S. Cl. .................. 604/891.1; 424/422; 604/507

(58) Field of Classification Search ............. 424/400, 424/408, 409, 417, 422, 423, 425, 426, 450, 424/451; 604/890.1, 507, 891.1; 623/1.1, 623/1.11, 1.36, 1.42; 606/195
See application file for complete search history.

(56) References Cited

U.S. PATENT DOCUMENTS

| | | | | |
|---|---|---|---|---|
| 3,797,485 A * | 3/1974 | Urquhart | ............... | 604/288.04 |
| 4,457,752 A * | 7/1984 | Vadasz | ....................... | 604/135 |
| 4,487,603 A * | 12/1984 | Harris | ....................... | 604/152 |
| 5,030,216 A * | 7/1991 | Theeuwes et al. | ....... | 604/892.1 |
| 5,041,107 A * | 8/1991 | Heil, Jr. | .................... | 604/891.1 |
| 5,410,016 A * | 4/1995 | Hubbell et al. | ............ | 528/354 |
| 5,538,504 A | 7/1996 | Linden et al. | | |
| 5,670,161 A | 9/1997 | Healy et al. | | |
| 5,733,871 A * | 3/1998 | Alps et al. | .................... | 514/12 |
| 5,834,449 A | 11/1998 | Thompson et al. | | |
| 6,139,520 A * | 10/2000 | McCrory et al. | ............ | 604/60 |
| 6,159,239 A | 12/2000 | Greenhalgh | | |
| 6,190,353 B1 | 2/2001 | Makower et al. | | |
| 6,272,370 B1* | 8/2001 | Gillies et al. | ............... | 600/411 |
| 6,302,870 B1 | 10/2001 | Jacobsen et al. | | |
| 6,344,035 B1 | 2/2002 | Chudzik et al. | | |
| 6,348,050 B1 | 2/2002 | Hartlaub | | |
| 6,364,903 B2 | 4/2002 | Tseng et al. | | |
| 6,368,346 B1 | 4/2002 | Jadhav | | |
| 6,371,970 B1 | 4/2002 | Khosravi et al. | | |
| 6,376,742 B1 | 4/2002 | Zdrahala et al. | | |

(Continued)

FOREIGN PATENT DOCUMENTS

WO WO-02/15824 A2 2/2002

OTHER PUBLICATIONS

"Beta-Blockers (Beta-Adrenergic Blocking Drugs)." *Texas Heart Institute Heart Information Center*. Mar. 18, 2003 <http://www.tmc.edu/thi/betameds.html>.

(Continued)

*Primary Examiner*—Sharon E. Kennedy
(74) *Attorney, Agent, or Firm*—Louis C. Cullman; Sally Brashoars (57) ABSTRACT

A method and device for the treatment of an aneurysm are provided. Different therapeutic agents are delivered to the aneurysmal site by a reservoir and delivery means in a localized, and, in some embodiments, time-released regimen, to treat, limit and reduce the severity of the aneurysm.

3 Claims, 10 Drawing Sheets

U.S. PATENT DOCUMENTS

| | | | |
|---|---|---|---|
| 6,387,121 | B1 | 5/2002 | Alt |
| 6,451,373 | B1 | 9/2002 | Hossainy et al. |
| 6,506,410 | B1 | 1/2003 | Park et al. |
| 6,514,515 | B1 | 2/2003 | Williams |
| 6,531,154 | B1 | 3/2003 | Mathiowitz et al. |
| 6,666,882 | B1* | 12/2003 | Bose et al. ............... 623/1.15 |
| 6,960,352 | B2* | 11/2005 | Noujaim et al. ........... 424/423 |
| 2002/0065542 | A1* | 5/2002 | Lax et al. ..................... 607/99 |
| 2002/0065546 | A1 | 5/2002 | Machan et al. |
| 2003/0014075 | A1* | 1/2003 | Rosenbluth et al. ........ 606/213 |
| 2003/0204246 | A1* | 10/2003 | Chu et al. .................. 623/1.23 |

OTHER PUBLICATIONS

"Beta Blockers." *Cardiac Consultants*. Mar. 18, 2003 <http://www.cardiacconsultants.com/beta.htm>.

"Beta Blockers (Beta-Adrenergic Bockers, Beta 1 Blockers, Beta 2 Blockers, B-Blockers)." *HeartCenterOnline*, Mar. 18, 2003 <http://www.heartcenteronline.com/myheartdr/common/articles.cfm?ARTID=331>.

"Beta-blocker." *Bartleby.com*. Mar. 18, 2003 <http://www.bartleby.com/65/be/beta-b.html>.

Slaiby, Jeffrey M. et al. "Expansion of aortic aneurysms is reduced by proparanolol in a hypertensive rat model." *Journal of Vascular Surgery*. Jan. 21, 2002 <http://www.harcourthealth.com/scripts/om.dll/serve?action=search DB&searchDBfor=art&a...>.

Vine, N. et al. "Metalloproteinases in degenerative aortic disease." *Clinical Science* 1991, 81: 233-239.

Goodman, Louis Sanford and Albert Gilman. *The Pharmacological Basis of Therapeutics*, New York: McGraw-Hill, 2001.

Jackson, Edwin K. "Renin and Angiotensin." 809-835.

Liao, Shixiong et al. "Suppression of experimental abdominal aortic aneurysms in the rat by treatment with angiotensin-converting enzyme inhibitors." *Journal of Vascular Surgery*. May 2001, 33, No. 5: 1057-1064.

Chaikof, Elliot L. et al. "Biomaterials and Scaffolds in Reparative Medicine." *Annals New York Academy of Sciences* 2002, 961: 96-105.

Griffith, Linda G. "Emerging Design Principles in Biomaterials and Scaffolds or Tissue Engineering." *Annals New York Academy of Sciences* 2002, 961: 83-95.

Ochoa, Erin R. et al. "An Overview of the Pathology and Approaches to Tissue Engineering." *Annals New York Academy of Sciences* 2002, 979: 10-26.

US 6,348,062, 02/2002, Hopkins et al. (withdrawn)

* cited by examiner

DELIVERY OF THERAPEUTICS TO TREAT ANEURYSMS

BACKGROUND OF THE INVENTION

Description of the Related Art

Aneurysm, the enlargement of a blood vessel at a specific location—at times to the point where rupture of the blood vessel is imminent—has been treated in the past by surgical intervention techniques, where the affected portion of the blood vessel is removed or bypassed so that the vessel lumen is replaced by a synthetic graft. This treatment regimen is highly invasive, typically requiring a multiple day postoperative hospital stay, as well as several months of recuperative time.

Basically, aortic aneurysms are classified according to where they are located along the aorta. A thoracic aortic aneurysm is located along the segment of the aorta that passes through the chest, and an abdominal aortic aneurysm is located along the segment of the aorta that travels through the abdomen. In addition to the aorta, any other large blood vessel in the body may produce aneurysms, including those that provide blood to the lower extremities, heart or brain.

Prophylactic methods for preventing the formation of aneurysms tend to rely on reducing blood pressure in an effort to reduce mechanical stress on the blood vessels. These methods involve drugs that can have undesirable side effects, e.g., kidney or liver damage, especially over long-term use.

Typically, surgical intervention for aneurysm repair is not indicated until the blood vessel diameter at the aneurysmal site expands to 200 to 300% of its normal diameter. Below this threshold, the normal course of treatment has been to monitor the site, and if the diameter of the blood vessel wall at the aneurysmal site continues to expand beyond an undesirable threshold diameter, intervene surgically. Through numerous studies performed during the past decade, many of which were summarized by Thompson et al. in *Curr. Probl. Surg.*, 39, 93 (2002), the basic knowledge of aneurysm disease has increased significantly. Given the fact that several pharmacological strategies, e.g., cyclooxygenase-2 (COX-2) inhibitors, tissue inhibitors of matrix metalloproteinases (MMP), and anti-inflammatories can reduce the severity and/or progression of an aneurysm in animal models, these approaches may also be able to limit the rate of aneurysm growth in humans.

Based on the current knowledge of the causes of aneurysms, MMP inhibition has been proposed as a potential therapeutic approach to treatment. Typical treatment requires the use of systemic MMP inhibitors, either orally, intra-muscularly or intravenously introduced, in a dosage sufficient to ensure that the quantity of agent reaching the aneurysm is sufficient to affect level of the elastin-attacking protein. For example, doxycycline could inhibit aneurysm growth in humans (see *J. Vasc. Surg.*, 31, 325 (2000)); however, the side effects of doxycycline, including the likelihood of the patient developing doxycycline resistant bacteria as a result of long term doxycycline treatment, dictate that doxycycline treatment in high doses may be only a short term solution to the problem of aneurysm growth. Other approaches to treat aneurysms are the use of anti-inflammatory agents, including COX-2 inhibitors (see *Circulation*, 100, 48 (1999)), angiotensin-converting enzyme (ACE) inhibitors (see *J. Vasc. Surg.*, 33, 1057 (2001)), nitric oxide synthase (NOS) inhibitors (see *Ann. Vasc. Surg.*, 16, 65 (2002)), and antioxidants.

In view of the above considerations, it is clear that the present methods to treat aneurysms have limitations. Moreover, there is no practical pharmacological method available to prevent the aneurysm formation, without having to worry about the side effects of the drugs used, though U.S. Pat. No. 5,834,449 employs the use of a tetracycline compound having no antimicrobial activity which could limit drug associated side effects.

Thus, there exists a need to treat an aneurysmal site with therapeutic agents so as to reduce the severity and/or the progression of the aneurysm and the risk of aneurysm rupture, tear or other failure. Therefore, there exists a need in the art to develop additional treatment regimens, particularly non-invasive or minimally invasive localized techniques, which may be used to reduce the severity of an aneurysm.

SUMMARY OF THE INVENTION

Devices and methods according to the present invention provide localized, and in some embodiments, time-release application of therapeutic agents useful to reduce the severity and the progression of an aneurysm. One embodiment according to the invention includes the administration of one or more therapeutic agents selected from a class of therapeutic agents which have been shown to block or inhibit the formation of biochemical compounds found in aneurysmal sites. The therapeutic agents may include matrix metalloproteinase (MMP) inhibitors, antibiotics such as doxycycline and tetracycline, cyclooxygenase-2 (COX-2) inhibitors, angiotensin-converting enzyme (ACE) inhibitors, glucocorticoids, beta blockers, nitric oxide synthase (NOS) inhibitors, antioxidants, non-steroidal anti-inflammatory drugs (NSAIDs) and cellular adhesion molecules (CAMs), and combinations of these. The agents preferably are localized to the aneurysmal site by the placement of a therapeutic delivery reservoir that is comprised of, or within which is provided, a carrier containing and capable of dosing over time the therapeutic agents. Thus, the reservoir may contain a carrier comprising a therapeutic agent, or the reservoir itself may comprise the therapeutic agent. The materials to be used for such a reservoir and/or carrier can be synthetic polymers, natural polymers, inorganics, and combinations of these.

The physical form of the drug-loaded reservoir or carrier can take the form of a sheet, a slab, a gel, a mass with various configurations, capsules, pellets or combinations of these, and the carrier, if present, may take the form of microparticles, nanoparticles, a liquid or combinations of these. In one embodiment the reservoir is used in conjunction with a stent or stent graft. A stent graft may be used to isolate the aneurysmal region of the blood vessel from blood flow so that the agent may be delivered directly to the aneurysmal blood vessel site, yet not enter the bloodstream directly. This can be accomplished by implanting the reservoir at the aneurysmal site adjacent the stent graft or the reservoir may utilize a pump or other mechanical element to distribute or deliver the therapeutic agent to the aneurysmal site. The invention further includes methods of delivering a therapeutic agent to an aneurysmal site utilizing the reservoir.

BRIEF DESCRIPTION OF THE DRAWINGS

So that the above-recited features according to the present invention can be understood in detail, a more particular description of certain aspects according to the invention, briefly summarized above, may be had by reference to embodiments, some of which are illustrated in the appended drawings. It is to be noted, however, that the appended drawings illustrate only a limited number of embodiments and are therefore not to be considered limiting of its scope as these will be known and understood to those with skill in the art.

FIG. 8 shows yet another embodiment according to the present invention. In FIG. 8, the aneurysmal site is in cross-section and the peri-aneurysmal device is not;

FIG. 9A-C show exemplary embodiments of a device according to the present invention.

DETAILED DESCRIPTION

Figure 1:
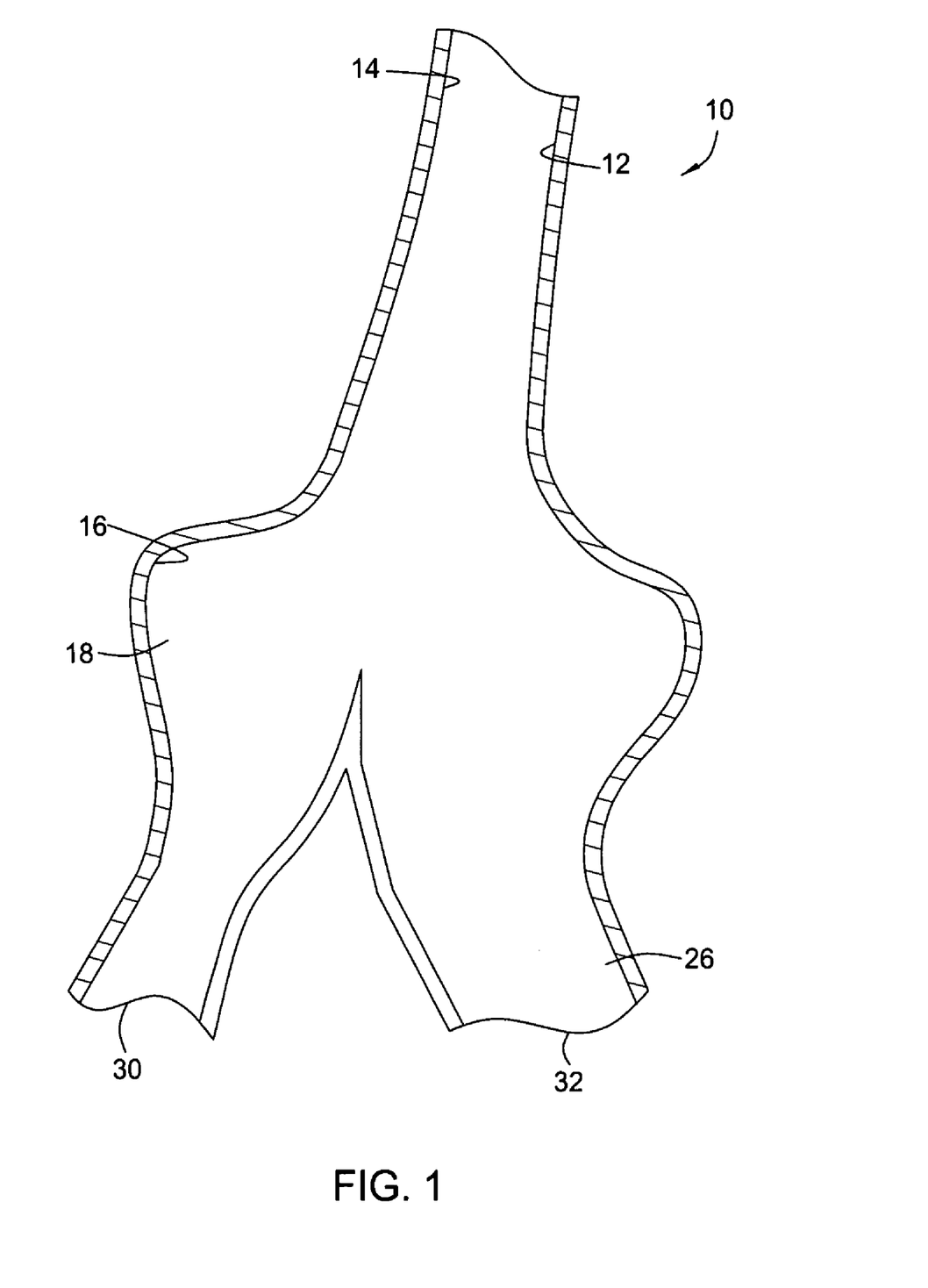
FIG. 1 is a sectional view of an ascending aorta with an aneurysm located therein.

A reservoir is provided to deliver locally therapeutic agents at the site of an aneurysm—in some embodiments, in a time-release formulation. Referring first to FIG. 1, there is shown, in section, an aneurysmal blood vessel, in this instance an aneurysm in an abdominal aorta 10. Aorta 10 includes a wall 12, having a healthy portion 14 and an aneurysmal wall portion 16, where the aneurysmal wall portion 16 occurs where the aorta has a diameter substantially larger than it does where the wall portion 14 occurs. Aneurysmal portion 16 forms an aneurysmal bulge or sac 18, where the extracellular matrix of the aortic vessel wall 12 is degraded, preventing the aortic wall 12 at the aneurysmal portion 16 from holding the aorta at its healthy diameter against the pressure of blood. A bifurcation of the vessel is seen at 30 and 32.

Where the aneurysmal sac 18 has progressed to a diameter on the order of twice the diameter of the healthy aortic wall 14, intervention to prevent rupture of the aneurysm may be dictated. Surgical intervention can include highly invasive procedures, where the section of the aorta undergoing the aneurysmal event is removed completely, and a synthetic graft is sewn in place between the severed ends of the aorta 10 or the vessel tissue is closed around an installed graft. Alternatively intervention may encompass exclusion of the aneurysmal sac 18 by placement of an exclusion device such as a stent graft.

Figure 2:
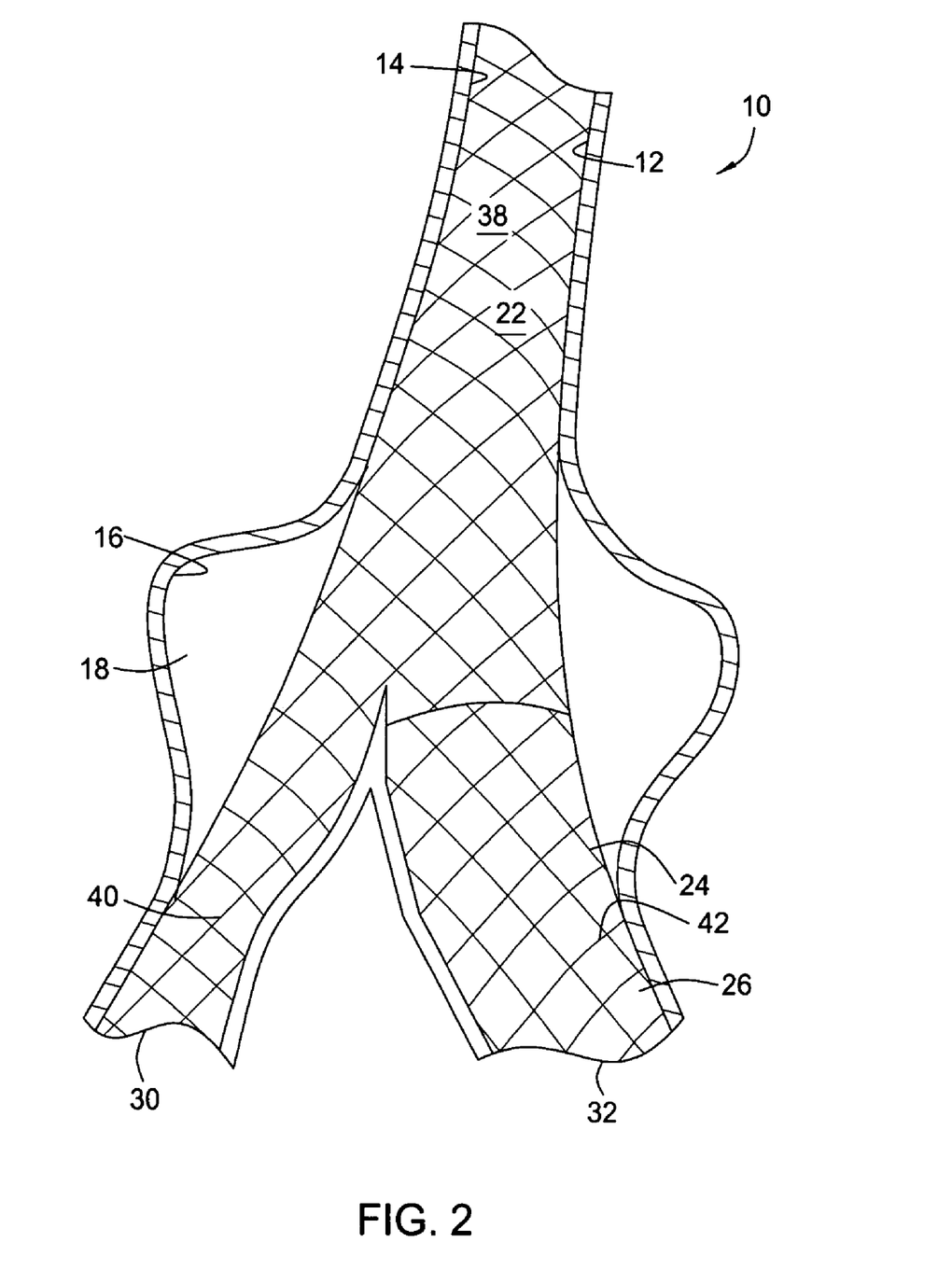
FIG. 2 is the sectional view of the ascending aorta of FIG. 1, with a stent graft placed in the area of the aneurysm.

FIG. 2 is a sectional view of an abdominal aorta with an aneurysmal site where a stent graft 22 has been inserted to exclude the aneurysmal portion from blood flow. Here, note again an abdominal aorta 10, including a wall 12, with a healthy wall portion 14 and an aneurysmal wall portion 16. Aneurysmal wall portion 16 forms an aneurysmal bulge or sac 18. A stent graft 22 typically includes a stent portion 24, having a rigid yet collapsible construction (here in a grid pattern), to which a graft portion 26 is sewn or attached. The stent portion 24 provides a tubular body having a support capability sufficient to hold the graft portion 26 in an open position across the aneurysmal sac 18, such that the opposed ends are received and sealed against portions 14 of the of the aorta. The graft portions 26 and 38 block the passage of blood into the aneurysmal sac 18, and provide a conduit for blood flow past the aneurysmal sac 18.

Although the stent graft 22 provides an exclusionary environment through which blood may flow past the aneurysmal sac 18, there remains a need to treat the aneurysmal sac 18. In particular, it is known that fresh blood may leak into the aneurysmal sac 18 region despite the presence of stent graft 22, leading to further breakdown in the extracellular matrix and the aneurysmal vessel. If this occurs, the excluded aneurysmal vessel may rupture leading to patient morbidity, which, if left untreated, will lead to mortality. Therefore, there remains a need to treat the aneurysmal sac further in addition to using an excluding device or as an alternative to using an excluding device.

Thus, the one or more therapeutic agents described herein, infra, are provided in a reservoir that delivers the therapeutic agent to an aneurysmal site. The reservoir may, in some embodiments, be used with an excluding device or intravascular repair vehicle, for example, the stent graft 22 shown in FIG. 2. Referring back to FIG. 2, the placement of the stent graft 22 in the aorta 10 is a technique well known to those skilled in the art, and essentially includes the opening of a blood vessel in the leg, and the insertion of the stent graft 22 contained in a catheter into the vessel, guiding the catheter through the vessel, and deploying the stent graft 22 in a position spanning the aneurysmal sac 18. Depending on the form and composition of the reservoir, the reservoir and its contents may be delivered to its position by catheter, or by surgical means.

Although the bifurcated stent graft 22 is shown in its fully assembled and positioned state, it is to be understood that the bifurcated stent graft 22 typically comprise three protion, a trunk portion 38, located in abdominal aorta 10, connecting to two minor diameter leg portions 40, 42 that fit into the iliac arteries 30 and 32. In one embodiment, the bifurcated stent graft 22 is configured such that each portion 38, 40 and 42 includes graft portion 26, supported externally by a tubular metal stent portion 24 that expands to a pre-established diameter when placed in the aorta 10. When assembled in place, the entire stent graft 22 spans the aneurysmal sac 18 in the aorta 10, to seal the aneurysmal portion of the aorta 10 from blood flowing through the aorta 10.

Figure 3:
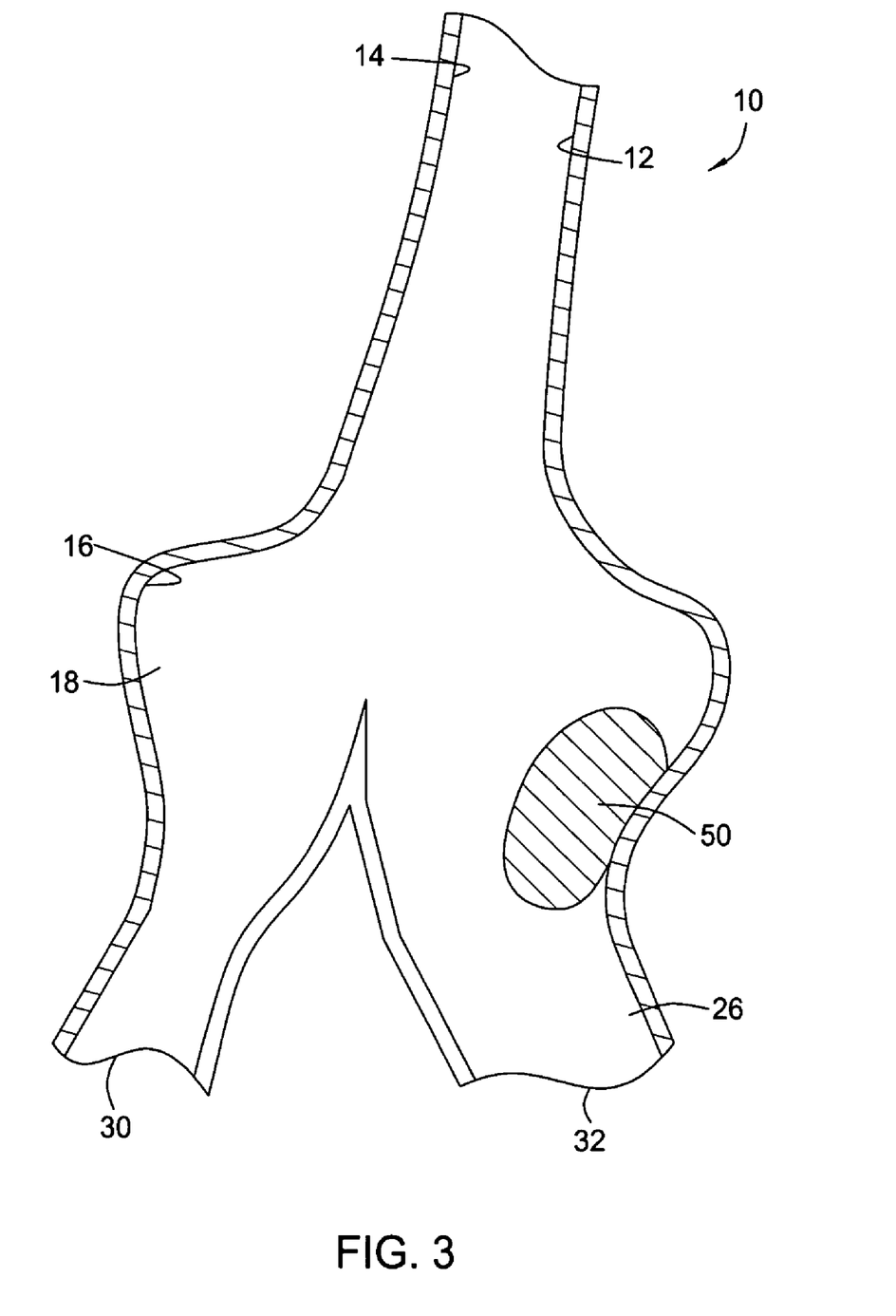
FIG. 3 shows one embodiment of a device according to the present invention located at and providing therapeutics to an aneurysmal site.

Turning to FIG. 3, there is shown an abdominal aorta 10, including a wall 12, with a healthy wall portion 14 and an aneurysmal wall portion 16. Aneurysmal wall portion 16 forms an aneurysmal bulge or sac 18. A bifurcation of the vessel is shown at 30 and 32. One embodiment of a therapeutic delivery reservoir 50 is shown placed within the aneurysmal bulge or sac 18 so as to deliver one or more therapeutic agents to the aneurysmal site. The reservoir 50 adheres to the site of the aneurysmal wall 16 of aorta 10 through a glue (for example, water activated adhesive, such as ethyl-cyanocylate) or hook(s) on the surface of the reservoir. Alternatively, the reservoir can be positioned by a stent in the blood vessel. In one aspect of this embodiment, the reservoir itself acts as a carrier releasing the one or more therapeutic agents. In such an embodiment, the reservoir may comprise a biodegradable polymer (discussed infra)

formulated with the one or more therapeutic agents. If the reservoir itself is not the carrier, in another aspect the reservoir may comprise a mesh or porous structure that allows the free passage of fluids therethrough, where a carrier within the reservoir comprises, e.g., a polymer and the therapeutic agent. In such an aspect, the reservoir may or may not be biodegradable. In yet another aspect of this embodiment, the reservoir may be a closed system but include a pump suitable for delivering the one or more therapeutic agents contained inside the reservoir with the carrier being no more than a solvent for the one or more therapeutic agents. In such an aspect, the pump may be a mechanical, electrical, or osmotic pump. In some aspects of this embodiment, the reservoir is biodegradable. In other aspects, the reservoir is not biodegradable and may be refilled periodically by a needle, catheter or other means known in the art.

Figure 4:
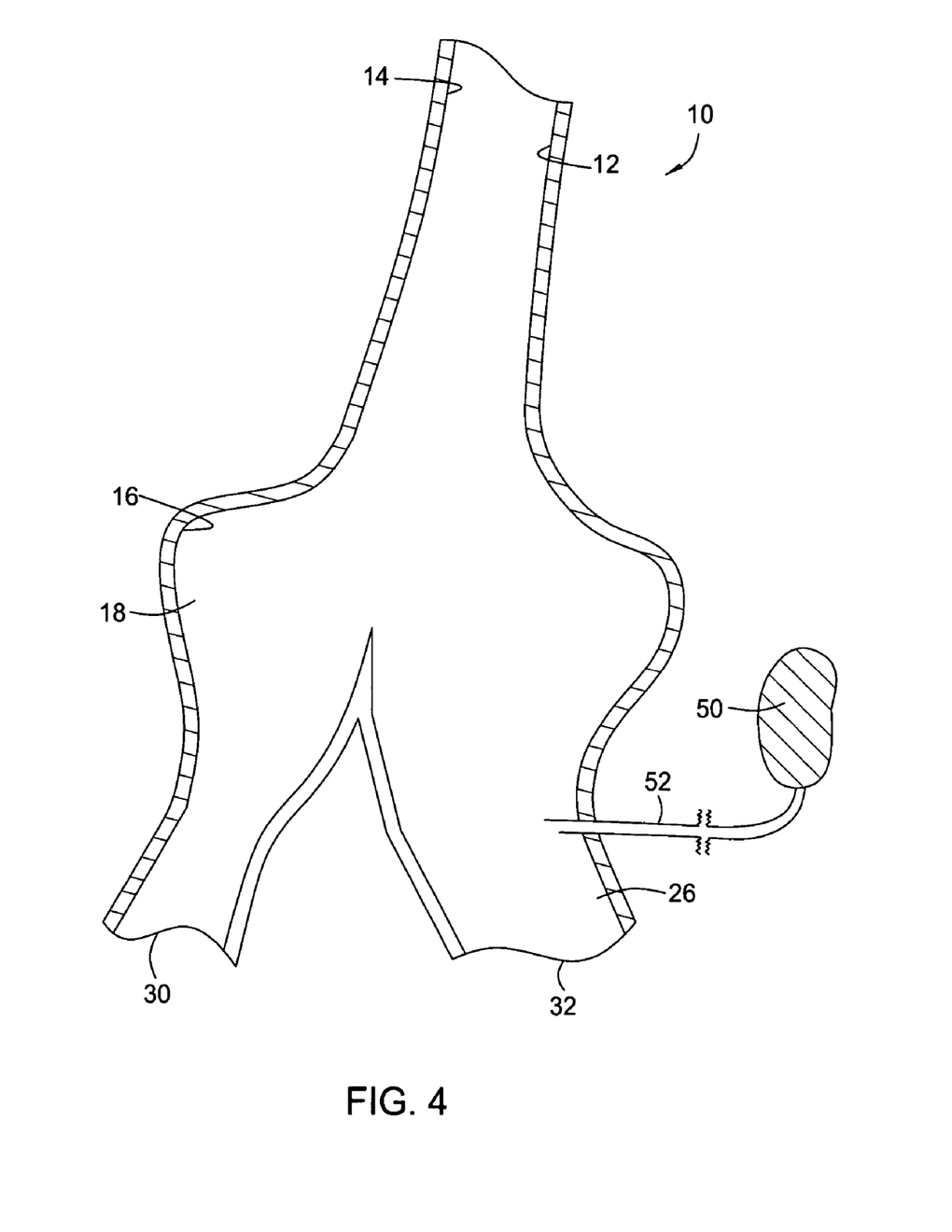
FIG. 4 shows another embodiment of a device according to the present invention providing therapeutics to an aneurysmal site.

FIG. 4 shows yet another embodiment of a device according to the present invention. FIG. 4 shows an abdominal aorta 10, including a wall 12, with a healthy wall portion 14, an aneurysmal wall portion 16, an aneurysmal bulge 18, and bifurcation of the vessel at 30 and 32. In FIG. 4, an alternative embodiment of the therapeutic delivery reservoir 50 is shown placed outside aneurysmal site, with a delivery means such as a tube of various configurations and/or formulations delivering the one or more therapeutic agents to the aneurysmal site. In one aspect of this embodiment, the reservoir would be a closed system including a pump suitable for delivering the one or more therapeutic agents contained inside the reservoir. In such an aspect, the pump may be a mechanical, electrical, or osmotic pump, and may be refilled periodically by a needle, catheter or other means known in the art.

Figure 5:
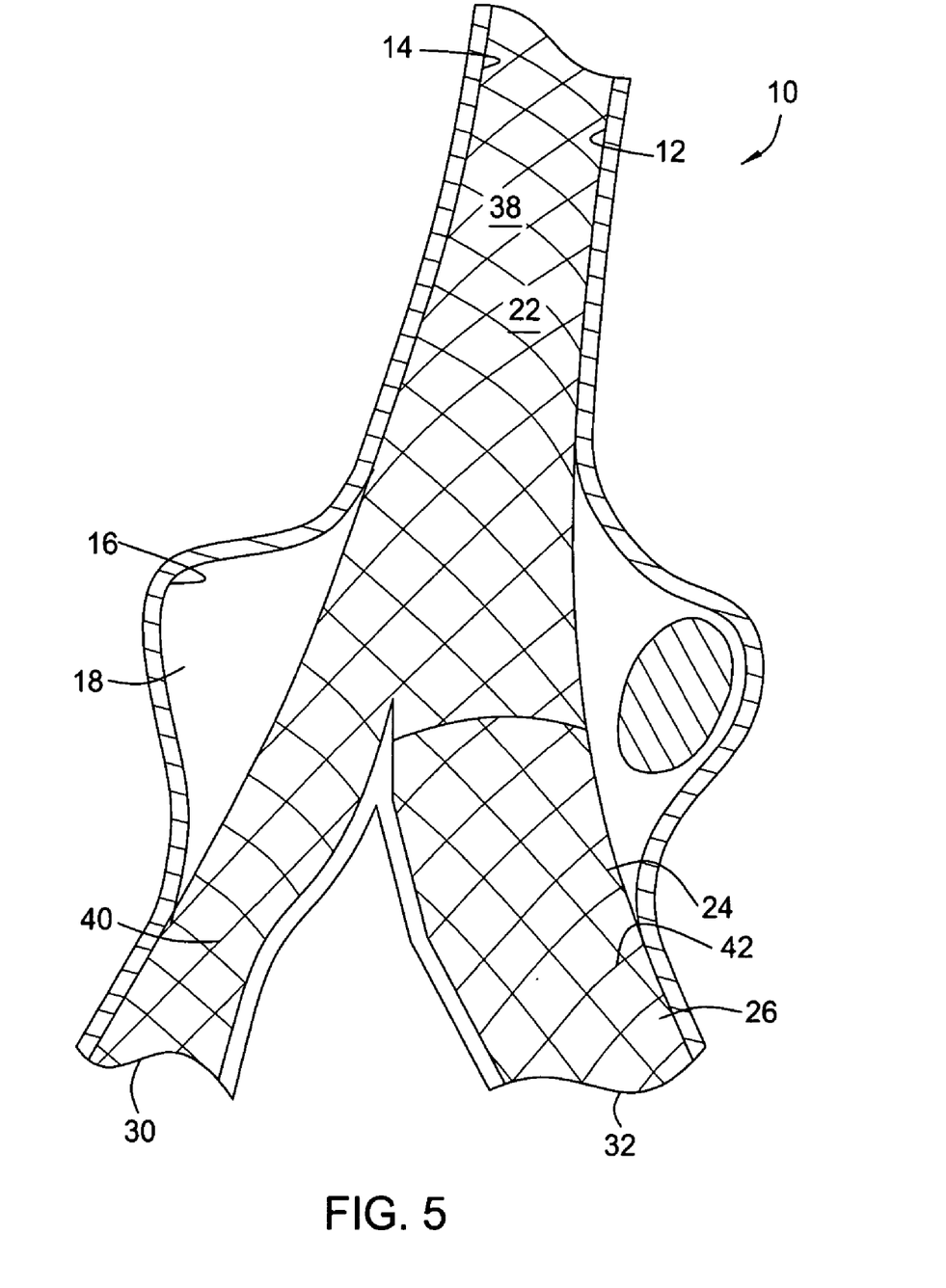
FIG. 5 shows another embodiment of a device according to the present invention located at and providing therapeutics to an aneurysmal site.

FIG. 5 shows yet another embodiment of a therapeutic delivery reservoir according to the present invention. In this case, the reservoir is used in conjunction with a stent graft 22 in the aorta 10. As with the device of FIG. 3, the reservoir itself may act as a carrier releasing the one or more therapeutic agents, where the reservoir comprises a biodegradable polymer (discussed infra) formulated with the one or more therapeutic agents. If the reservoir itself is not the carrier, in a second aspect the reservoir may comprise a mesh or porous structure that allows the free passage of fluids therethrough, where a carrier within the reservoir comprises the therapeutic agent. In such an aspect, the reservoir may or may not be biodegradable. In a third aspect of this embodiment, the reservoir may be a closed system but, as described previously, include a pump or other means suitable for delivering the one or more therapeutic agents contained inside the reservoir to the aneurysmal site. Again, the pump may be a mechanical, electrical, or osmotic pump. In some aspects of this embodiment, the reservoir is biodegradable. In other aspects, the reservoir is not biodegradable and may be refilled periodically by a needle, catheter or other means known in the art as necessary.

Figure 6:
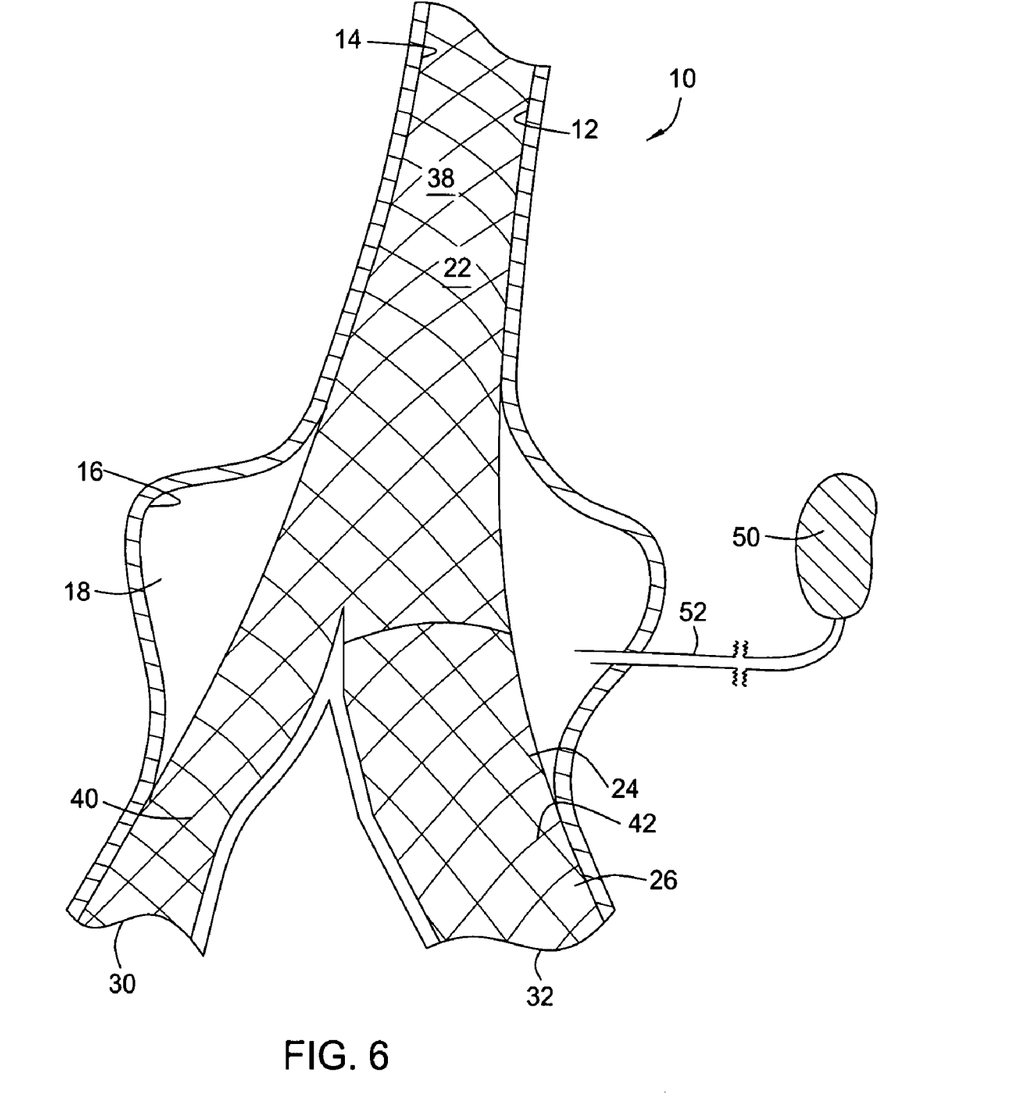
FIG. 6 shows another embodiment of a device according to the present invention providing therapeutics to an aneurysmal site.

FIG. 6 is similar to FIG. 4; however, in this embodiment the therapeutic delivery reservoir is used in conjunction with a stent graft 22 in the aorta 10. As with FIG. 4, the therapeutic delivery reservoir 50 is shown placed outside aneurysmal site, with a delivery means delivering the one or more therapeutic agents to the aneurysmal site. In one aspect of this embodiment, the reservoir would be a closed system including a pump suitable for delivering the one or more therapeutic agents contained inside the reservoir. In such an aspect, the pump may be a mechanical, electrical, or osmotic pump, and may be refilled periodically as necessary by a needle, catheter or other means known in the art.

Figure 7:
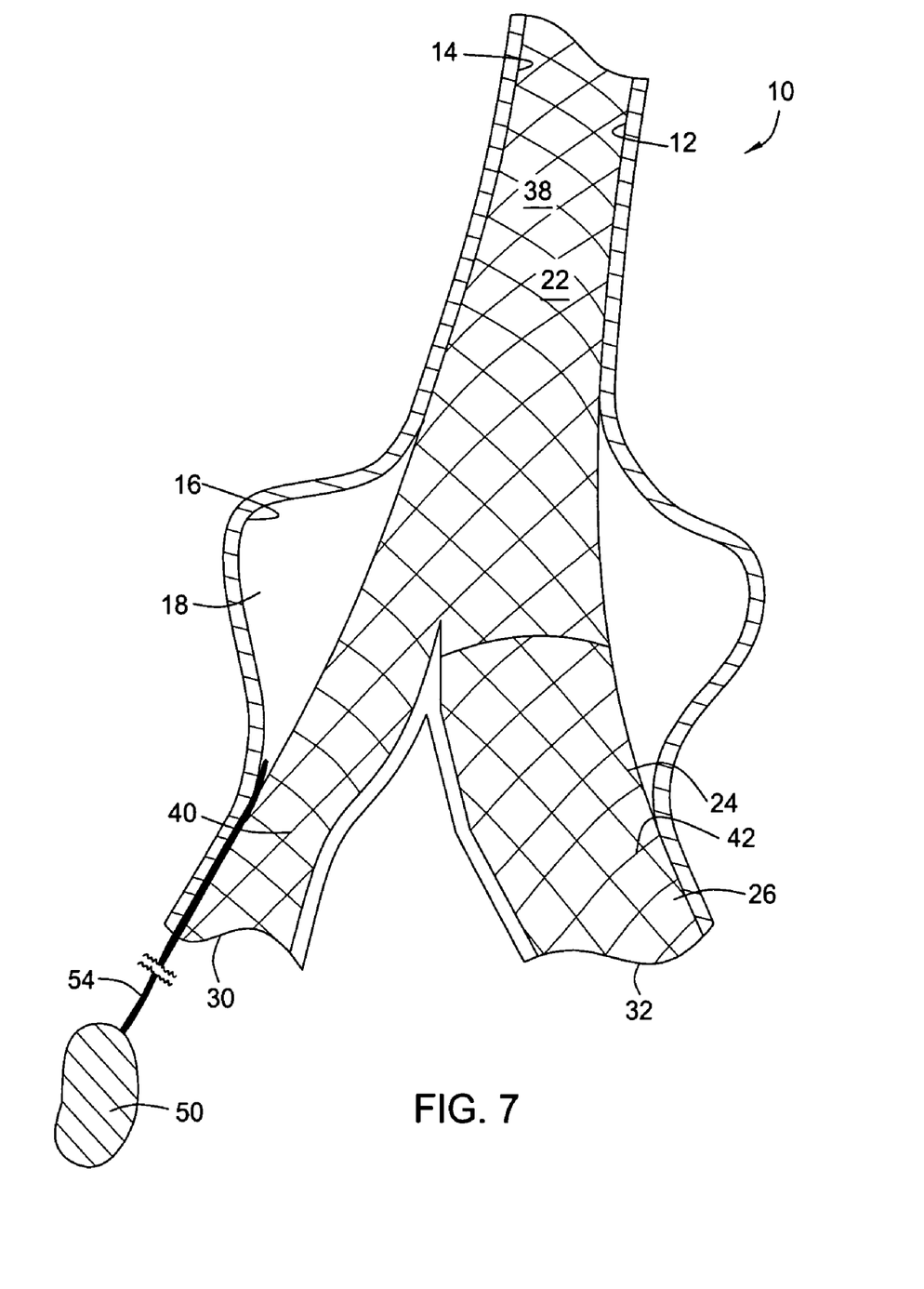
FIG. 7 shows another embodiment of a device according to the present invention providing therapeutics to an aneurysmal site.

FIG. 7 shows yet another embodiment of the therapeutic delivery reservoir 50. In this embodiment, the reservoir is located outside the aneurysmal site; however in this embodiment, the one or more therapeutic agents is delivered to the aneurysmal site by a catheter initially tracked along side the catheter that delivered the stent graft 22. Again, in this embodiment, a pump or other suitable device may be employed for delivering the one or more therapeutic agents contained inside the reservoir.

The reservoirs shown in the various embodiments in FIGS. 3 and 5 may be delivered to the site within the aneurysmal site by a catheter or other means known in the art. The reservoir shown in FIGS. 4, 6 and 7 located outside the aneurysmal site may be delivered by surgical implantation (including less invasive laparoscopic procedures) or by catheter or other appropriate means. The reservoirs are secured in the body by glue, hooks, sutures or a stent. Alternatively, in embodiments where the reservoir is not localized at the aneurysmal site, the reservoir may even be located outside the body.

Figure 8:
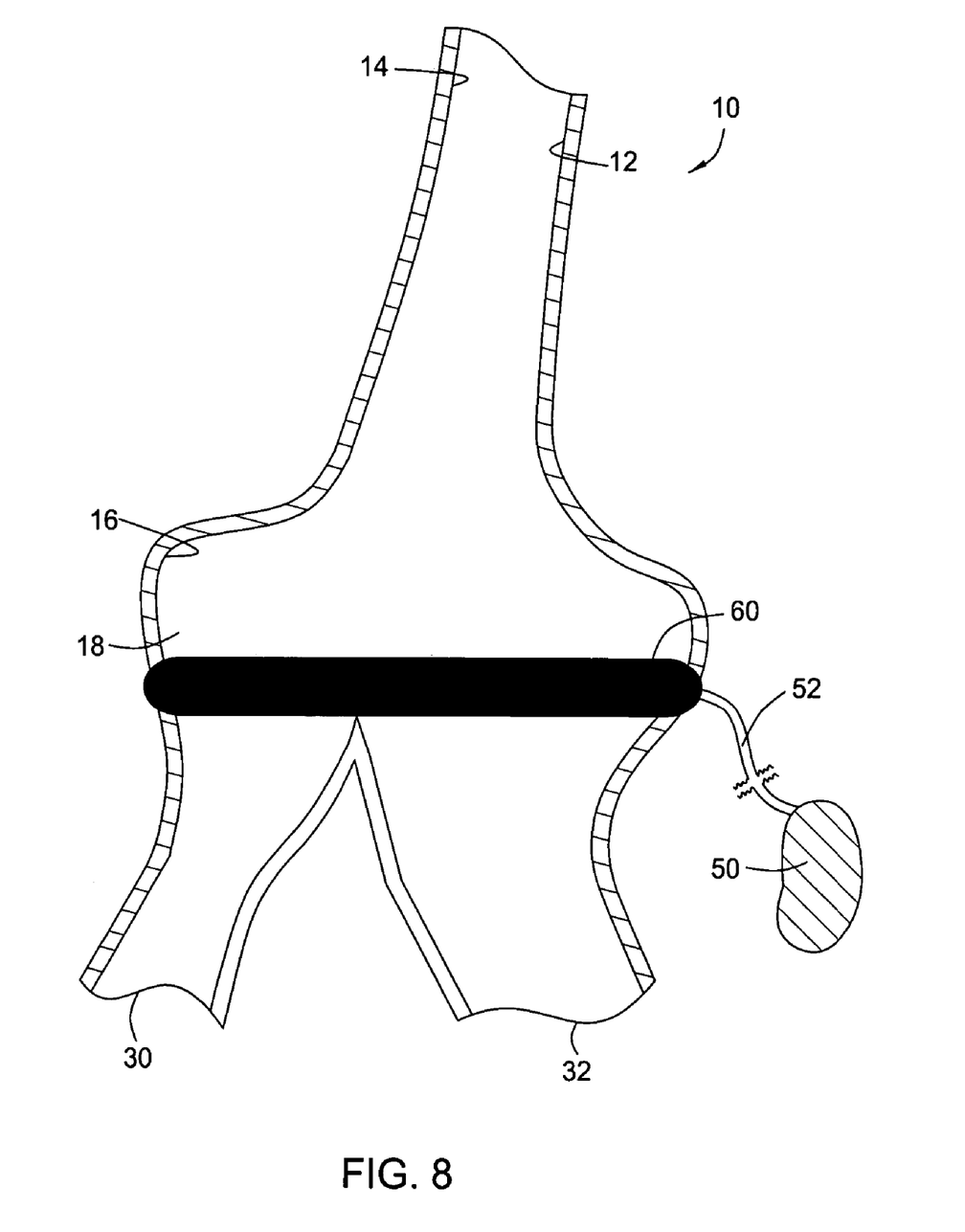
Figure 10:
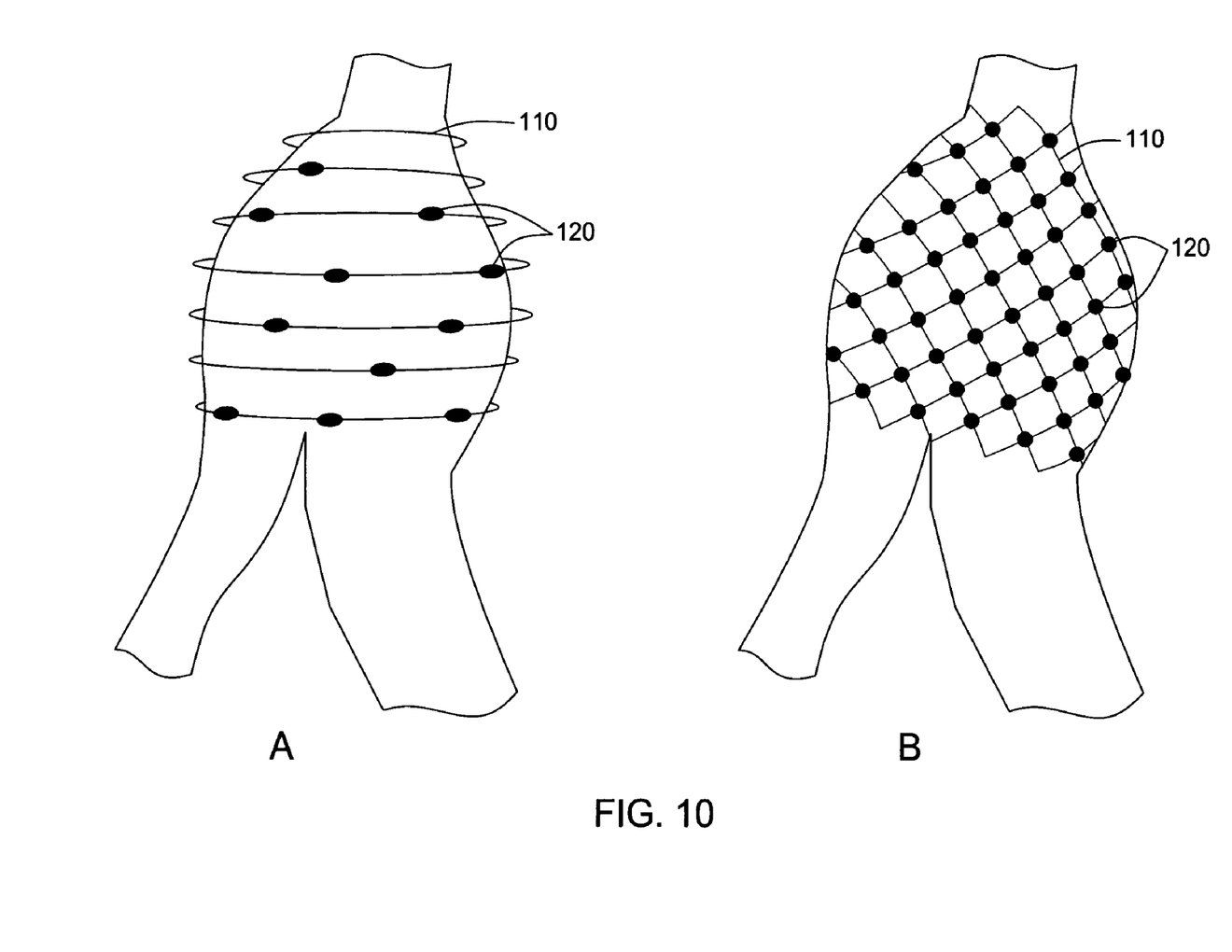
FIG. 10 shows two additional embodiments of a peri-aneurysmal delivery device.

FIG. 8 shows yet another embodiment of a reservoir according to the present invention. In this embodiment, the reservoir 50 is not located at the aneurysmal site, but delivers the one or more therapeutic agents to the aneurysmal site via tube 52 and a peri-aneurysmal device 60, for example, an absorbent delivery device such as polyvinyl alcohol foam. The reservoir 50 supplies the therapeutic agent to the tube 52, which delivers the therapeutic agent to the absorbent device 60, which in turn supplies the therapeutic agent to the aneurysmal site. In one aspect of this embodiment, the reservoir is located outside the body. Such a peri-aneurysmal device or multiple devices can be delivered to the patient by common surgical means (open surgery) or by laparoscopy. In addition, FIGS. 10A and B show two additional embodiments of a peri-aneurysmal delivery device according to the present invention. FIG. 10A shows a spiral configuration peri-aneurysmal device at 110, and FIG. 10B shows a diamond configuration peri-aneurysmal device at 110. At 120, there are capsules or reservoirs of therapeutic agent available for delivery on the outer wall of the aneurysmal site. In these embodiments, unlike FIG. 8, the reservoir itself comprises the therapeutic agent.

Figure 9:
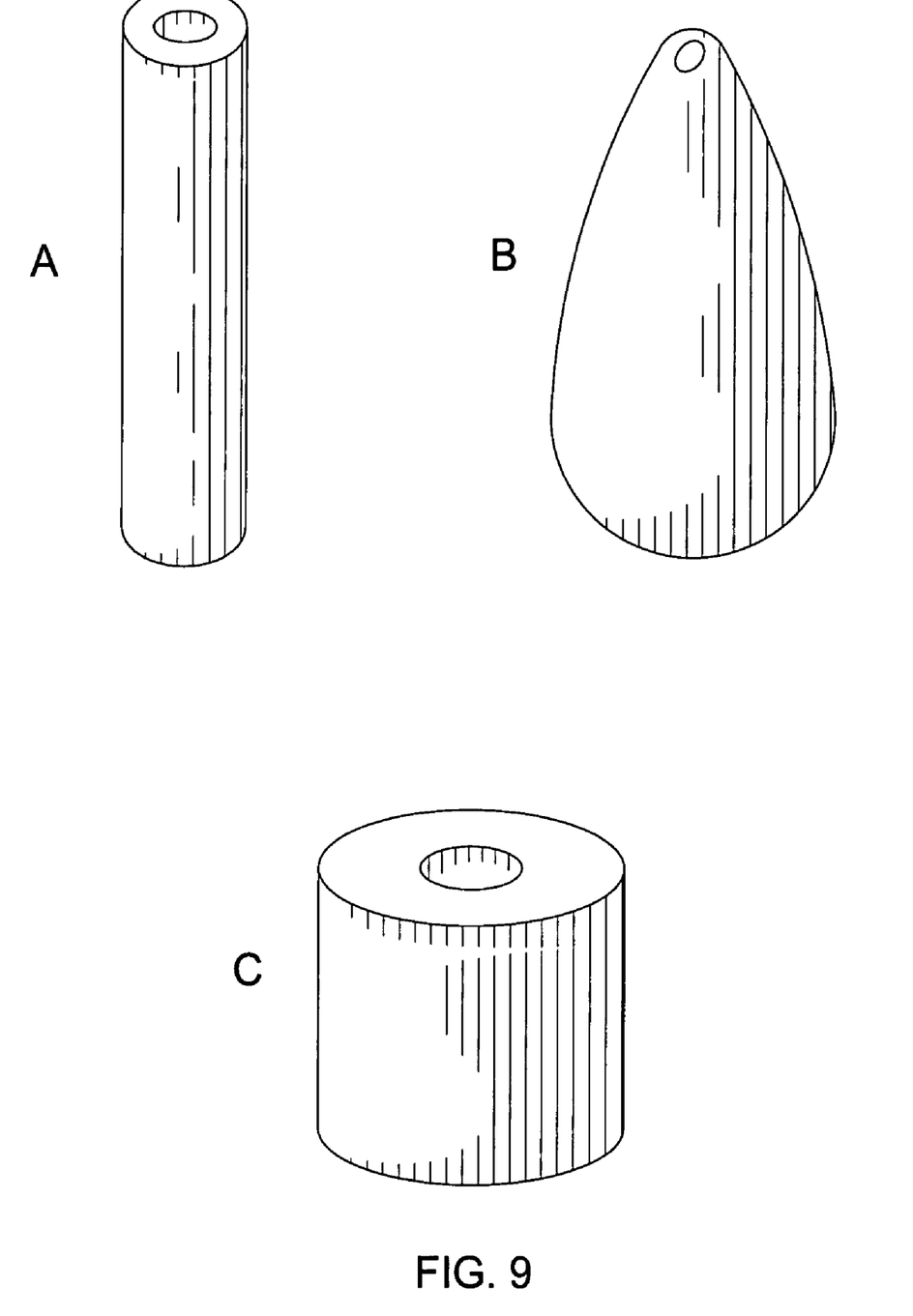

FIGS. 9A-C show various configurations that the reservoir may take. As stated previously, the reservoir may itself be formulated to deliver the one or more therapeutic agents; in which case the reservoir itself may take the form of, e.g., a sheet, a slab, a gel, a sponge, a mass with various configurations, capsules, pellets, or combinations of these. Alternatively, the reservoir may act as a vessel for a carrier formulated to deliver the one or more therapeutic agents. In such a case, the reservoir may be of any appropriate configuration that allows delivery of the one or more therapeutic agents, including cylindrical, spherical, oval, or irregular configurations. Also, more than one device can be used to deliver the same or different therapeutic agents.

As the figures demonstrate, the therapeutic delivery reservoir according to the present invention may be used with or without a stent graft or other exclusionary device. If the therapeutic delivery reservoir or delivery means is isolated by a stent graft from the blood passing through the aorta such as those seen in FIGS. 5, 6 and 7, the therapeutic agent is delivered into a relatively sealed environment where the blood and other fluids that may be in this region have a limited likelihood of being transmitted or passed from this region. Thus, the therapeutic agent will be released such that a maximum concentration of the agent or agents likely will be reached in this region alone, and are not delivered directly to the rest of the body. As a result, substantial quantities of the therapeutic agent remain in place at the aneurysmal site for a longer period of time, increasing efficacy of agent and without diffusion or release into the blood or other fluid. Such a localized delivery lessens the negative effects of systemic administration of the one or more therapeutics and requires a lesser quantity of therapeutic agent to be delivered.

Therapeutic agents according to the present invention are those that are known in the art that are useful in treating aneurysms or that reduce the likelihood of progression of aneurysms. Such agents include, for example, matrix metalloproteinase (MMP) inhibitors, antibiotics, cyclooxygenase-2 (COX-2) inhibitors, angiotensin-converting enzyme (ACE) inhibitors, glucocorticoids, beta blockers, nitric acid synthase (NOS) inhibitors, antioxidants and cellular adhesion molecules (CAMs). The therapeutic agent or agents are released over time in the aneurysmal location, reducing the likelihood of further dilation and increasing the likelihood of successful repair of the aneurysm. It is contemplated that the therapeutic agent or agents may be supplied to the aneurysmal site with an excluding device such as a stent graft. Since the therapeutic agents are delivered locally, the dosage necessary for and side effects associated with oral or intravascular delivery are reduced substantially.

The therapeutic agents used in certain embodiments are those known to inhibit or block the production of biochemical compounds known to be found in aneurysmal blood vessel locations, but which are found at much lower concentrations in healthy blood vessels. Such compounds are at least in part responsible for, or are initiators or catalysts of inflammation or the loss of structural support in blood vessels. Such inflammation or loss of structural integrity contributes to aneurysm formation and progression. In one embodiment, these therapeutic agents, when localized at the aneurysmal location, reduce the production of and/or occurrence of extracellular matrix-attacking proteins at the aneurysmal site. The therapeutic agents according to the present invention work through various mechanisms; for example, some work by altering biochemical pathways that produce compounds that cause inflammation, others work by inhibiting elastases, gelatinases or other proteinases or by preventing the adhesion of such molecules to the vascular cell wall.

For example, metalloproteinase 9 (MMP-9) is a protein that attacks elastin and collagen and causes the breakdown of the medial and adventitial tissue of the vasculature. Cyclooxygenase-2 or "COX-2" is known to synthesize prostaglandin E2 (PGE2), which has been found at increased levels in human abdominal aortic aneurysms. It is thought that the increased levels of PGE2 lead to the increased release of inflammatory cytokines, possibly the decreased synthesis of collagen and later MMP-9. Thus, if COX-2 or PGE2 is suppressed, then MMP-9 formation may also be suppressed further down the line. Therefore, an embodiment according to the present invention, in one aspect, provides inflammation and COX-2 inhibitors at the aneurysmal site.

The generation of cytokines may be limited by reducing the capability of COX-2 to produce PGE2. It is known that certain NSAIDs provide this function. For example, ketoralac tromethamine (Toradol) inhibits synthesis of progstaglandins including PGE2. In addition, other currently available NSAIDs, including indomethacin, ketorolac, ibuprofen and aspirin, among others, reduce inflammation at the aneurysmal site, which could potentially limit the ability of enzymes such as MMP-9 to enter into the extracellular matrix of the blood vessel and degrade structural proteins. Additionally, steroidal based anti-inflammatories, such as methylprednisolone, dexamethasone or sulfasalazine may be provided to reduce the inflammation at the aneurysmal site. Other suitable anti-inflammatory agents include cyclosporine A and azathioprine. Other types of suitable therapeutic agents may be anti-oxidants, such as curcumin, vitamins, and vitamin constituents, such as α-tocopherol and β-carotene.

Other COX-2 inhibitors include Celecoxib, Rofecoxib, Valdecoxib, Etoricoxib, and Parecoxib, all of which are available in pharmacological preparations. Additionally, COX-2 inhibition has been demonstrated from herbs such as green tea, ginger, turmeric, chamomile, Chinese goldthread, barberry, baikal skullcap, Japanese knotweed, rosemary, hops, feverfew, and oregano; and from other agents such as piroxican, mefenamic acid, meloxican, nimesulide, diclofenac, MF-tricyclide, raldecoxide, nambumetone, naproxen, herbimycin-A, and diaryl hydroxyfuranones. It is specifically contemplated that such additional COX-2 inhibiting materials may be formulated for use in an aneurysmal location.

One method of potently inhibiting MMPs is via a functional group capable of chelating the active site zinc ion strongly. Embodiments according to the present invention use one or more of the major classes of MMP inhibitor compounds: hydroxamic acids, carboxylic acids, thiols, phosphinic acids, and tetracyclines. Typical MMP inhibitors include N-biphenyl sulfonyl-phenylalanine hydroxamic acid; amines, amino acid derivatives and low molecular weight peptides containing an amide-bound oxal hydroxamic acid moiety; benzodiazepine; acyclic succinic acid-based compounds; oleic acid; cerivastatin; thiol compound MAG-283; tetracycline derivatives, such as tetracycline, doxycycline (Periostat®)), and 6-deoxy-6-demethyl-4-dedimethylamino-tetracycline (COL-3). Other suitable inhibitors include chelating agents, such as EDTA.

Another class of therapeutic agents useful in embodiments according to the present invention is the class of agents that limit the ability of leukocytes to adhere to the blood vessel wall, such as antibodies. Anti-adhesion molecules, such as anti-CD18 monoclonal antibody, limit the capability of leukocytes to attach to the blood vessel wall, thereby limiting inflammation and, therefore, aneurysm expansion.

Other therapeutic agents useful in the present invention are angiotensin-converting enzyme (ACE) inhibitors that potentially suppress the development of connective tissue destruction and modulate connective tissue remodeling. Such ACE inhibitors known in the art are captopril, enalapril, losartan and lisinopril and the active forms of several ACE inhibitor prodrugs on the market. Other agents such as the NOS inhibitor aminoguanidine are also useful in embodiments of the present invention.

Another class of therapeutic agent that finds utility in embodiments according to the present invention for inhibiting the progression or inducing the regression of a pre-existing aneurysm is beta blockers or beta adrenergic blocking agents. Beta blockers that may be used in the compounds and methods according to the present invention include acebutolol, atenolol, betaxolol, bisoprolol, carteolol, carvedilol, esmolol, labetolol, metoprolol, nadolol, penbutolol, pindolol, propranolol, and timolol, as well as other beta blockers known in the art.

As for the formulation of the reservoir and, if present, the carrier, the reservoir itself may be fashioned in a variety of forms with desired release characteristics and/or with specific desired properties. For example, the reservoir may be a solid or porous structure comprising a carrier polymer and the one or more therapeutic agents. In such a case, the reservoir may be biodegradable.

If the reservoir is not formulated with the one or more therapeutic agents, the therapeutic agents may be formulated with one or more carriers contained inside the reservoir. Such carriers may be fashioned to be in the form of a sheet, a slab, a gel, a capsule, a sponge, microparticles, nanoparticles, pellets, a liquid or combinations of these. For example, the reservoir may contain a polymeric gel comprising the therapeutic agent. Such a gel may be prepared by dissolving the polymer in an organic solvent in which the therapeutic agent or agents are either dissolved or dispersed, preferably in a time release fashion. In such a case, the carrier and therapeutic agent or agents are maintained within the reservoir, yet fluids and the agent are allowed to transport through the reservoir. In such an embodiment, the therapeutic delivery reservoir may be manufactured from a biocompatible material that is permeable to water and dissolved therapeutic agents, such as polyolefins (polypropylene, polyethylene), polyurethanes, silicones, polyesters (Dacron®) and fluorinated polyolefins (PTFE).

In addition, one or more than one therapeutic may be provided with more than one carrier for differing release characteristics. For example, a single therapeutic may be combined with two different carriers for both short- and long-term release characteristics. Alternatively, multiple therapeutics may be combined with different carriers to achieve varying release characteristics, or to optimize release parameters.

The reservoir/carrier formulation comprises a material to ensure a controlled, preferably sustained, release of the therapeutic agent. The materials to be used for such a formulation for the present invention preferably comprise one or more biocompatible polymers. If the reservoir is the carrier, the reservoir must be formulated to deliver the one or more therapeutic agents. If the reservoir is a vessel for the carrier, then the carrier must be formulated to deliver the one or more therapeutic agents, and the reservoir must be configured and formulated to be compatible with the carrier.

Thus, the therapeutic agent formulation comprises a reservoir alone or with a carrier, which, according to the present invention, may be made of synthetic polymers, natural polymers, inorganics or combinations of these. The polymers may be either biodegradable or non-biodegradable (biostable). Typical examples of biodegradable synthetic polymers are:

Aliphatic polyesters, such as poly(lactic acid), poly(glycolic acid), poly(lactic acid-co-glycolic acid), poly(ε-caprolactone), poly(trimethylene carbonate), polydioxanone and copolymers; poly(hydroxy butyrate) (Biopol®), poly(hydroxy valerate), poly(hydroxy butyrate-co-hydroxy valerate), poly(butylene succinate) (Bionolle®), poly(butylene adipate),
Polyanhydrides, such as poly(adipic anhydride), and poly (sebacic acid-co-1,3-bis(p-carboxyphenoxy)propane),
Poly(ortho ester)s,
Poly(ester amide)s, such as based on 1,4-butanediol, adipic acid, and 1,6-aminohexanoic acid (BAK 1095),
Poly(ester urethane)s,
Poly(ester anhydride)s,
Poly(ester carbonate)s, such as tyrosine-poly(alkylene oxide)-derived poly(ether carbonate)s,
Polyphosphazenes,
Polyarylates, such as tyrosine-derived polyarylates,
Poly(ether ester)s, such as poly(butylene terephthalate)-poly(ethylene glycol) copolymers (PolyActive®), poly (ε-caprolactone)-b-poly(ethylene glycol)) block copolymers, and poly(ethylene oxide)-b-poly(hydroxy butyrate) block copolymers.

If the reservoir itself is formulated with the one or more therapeutic agents, the reservoir may be biodegradable. If the reservoir is configured to be a vessel or receptacle for a carrier, then the carrier may be biodegradable. In some embodiments both the reservoir and the carrier may be biodegradable, with the reservoir being formulated to have a slower period of degradation.

On the other hand, if the reservoir is configured with a pump to deliver the one or more therapeutic agents, then the reservoir may be biostable. Examples of biostable synthetic polymers include:

Polyolefins, such as polyethylene, polypropylene,
Polyurethanes,
Fluorinated polyolefins, such as polytetrafluoroethylene (Teflon®),
Chlorinated polyolefins, such as poly(vinyl chloride),
Polyamides,
Acrylate polymers, such as poly(methyl methacrylate) and copolymers (Eudragit®)),
Acrylamide polymers, such as poly(N-isopropylacrylamide),
Vinyl polymers, such as poly(N-vinylpyrrolidone), poly (vinyl alcohol), poly(vinyl acetate), poly(ethylene-co-vinylacetate),
Polyacetals,
Polycarbonates,
Polyethers, such as based on poly(oxyethylene) and poly (oxypropylene) units (Pluronic®)),
Aromatic polyesters, such as poly(ethylene terephthalate) (Dacron®), poly(propylene terephthalate) (Sorona®)
Poly(ether ether ketone)s,
Polysulfones,
Silicone rubbers,
Thermosets, such as epoxies,
and Poly(ester imide)s In addition, the reservoir or carrier (if present) may be comprised of an inorganic compound. Representative examples of inorganics are:
Hydroxyapatite,
Tricalcium phosphate,
Silicates, such as Bioglass®, montmorillonite, and mica.

Also, natural polymers may be employed. Typical examples of natural polymers include albumin, collagen, gelatin, hyaluronic acid, starch, alginate, pectin, cellulose and cellulose derivatives (such as methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran, polysaccharides (such as sucrose acetate isobutyrate), and fibrinogen.

Additionally, materials as described herein also can be blended in various compositions as required.

The following Example demonstrates one exemplary device and method of treatment according to one embodiment of the present invention.

EXAMPLE

An aneurysm model was created in male Sprague Dawley rats by aortic porcine pancreatic elastase (PPE) infusion. Doxycycline was then delivered to the aneurysm site by means of a delivery reservoir, in this case a 2 mL osmotic pump (Model 2ML2, Alzet Osmotic Pumps, Cupertino, Calif.) connected to a polyethylene catheter. The osmotic pumps were pre-loaded with doxycycline in saline, and secured in a subcutaneous pocket. The polyethylene catheter delivered the doxycycline from the pump to the peri-aortic space. A porous, 1 mm thick sheet of polyvinyl alcohol foam was used as a peri-aortic wrap which acted to secure the tube to the aorta while absorbing the doxycycline and ensuring circumferential delivery of the drug.

The osmotic pump delivered therapeutics for 14 days. To assess serum drug concentration, rat tail-vein blood was drawn periodically over the 2 week time period. It was determined that the therapeutic delivery reservoir was able to successfully deliver the drug, releasing over 85% of the solution during treatment time, and maintaining 60-fold lower serum doxycycline dose levels than those demonstrated in comparable controls having doxycycline delivered via subcutaneous injection. Limitation of aneurysm expansion was comparable in both the local and subcutaneous delivery groups.

While the foregoing is directed to embodiments according to the present invention, other and further embodiments of the invention may be devised without departing from the basic scope thereof.

All references cited herein are to aid in the understanding of embodiments according to the invention, and are incorporated in their entireties for all purposes.

The invention claimed is:

1. An aneurismal tissue treatment device comprising:
at least one reservoir; and
at least one therapeutic agent within said reservoir;
wherein said reservoir is adapted for implantation external to an aneurysm site and delivers at least one therapeutic agent to said aneurismal tissue by means of a pump and tubing for the treatment of said aneurismal tissue; and
wherein said at least one therapeutic agent is selected from the group consisting of matrix metalloproteinase (MMP) inhibitors, antibiotics such as doxycycline and tetracycline, cyclooxygenase-2 (COX-2) inhibitors, angiotensin-converting enzyme (ACE) inhibitors, glucocorticoids, beta blockers, nitric oxide synthase (NOS) inhibitors, antioxidants, non-steroidal anti-inflammatory drugs (NSAIDs) and cellular adhesion molecules (CAMs), and combinations thereof.

2. The device of claim 1, wherein said pump is a mechanical, electrical, or osmotic pump.

3. The device of claim 1, wherein a first end of said tubing is in communication with said pump and a second end of said tubing is adapted to be located within the blood vessel lumen within or adjacent to the aneurysm sac.

* * * * *